United States Patent
Presser et al.

(10) Patent No.: US 10,098,653 B2
(45) Date of Patent: Oct. 16, 2018

(54) PORTABLE MICRODERMABRASION DEVICE WITH SWIVELING ERGONOMIC HANDLE

(71) Applicant: PRESSER DIRECT, LLC, Los Angeles, CA (US)

(72) Inventors: Mark Presser, Los Angeles, CA (US); Daniel S. C. Kwok, Kowloon (HK)

(73) Assignee: PRESSER DIRECT, LLC, Los Angeles, CA (US)

( * ) Notice: Subject to any disclaimer, the term of this patent is extended or adjusted under 35 U.S.C. 154(b) by 1044 days.

(21) Appl. No.: 14/462,480

(22) Filed: Aug. 18, 2014

(65) Prior Publication Data
US 2015/0051620 A1 Feb. 19, 2015

Related U.S. Application Data

(63) Continuation-in-part of application No. 29/477,018, filed on Dec. 18, 2013, now Pat. No. Des. 737,441.
(Continued)

(51) Int. Cl.
*A61B 17/32* (2006.01)
*A61B 17/54* (2006.01)
(Continued)

(52) U.S. Cl.
CPC .............. *A61B 17/32* (2013.01); *A61B 17/54* (2013.01); *A61B 2017/00398* (2013.01);
(Continued)

(58) Field of Classification Search
CPC ...... A61B 17/545; A61B 2017/320004; A61B 2017/00761; A61B 17/54; A61B 2017/2927; A61B 2017/2929; A61B 17/32
See application file for complete search history.

(56) References Cited

U.S. PATENT DOCUMENTS

| | | |
|---|---|---|
| D132,468 S | 10/1872 | Jacobson |
| 2,249,500 A | 7/1941 | Shirley et al. |

(Continued)

FOREIGN PATENT DOCUMENTS

| | | |
|---|---|---|
| DE | 3408819 | 11/1985 |
| DE | 3740902 | 12/1988 |
| EP | 0137711 | 4/1992 |

OTHER PUBLICATIONS

*Kelley West and Kelley West, Inc.* vs. *Ira Smolens et al.*, "Verified Complaint and Demand for Jury Trial," filled May 20, 2015, paragraph 10, p. 3.
(Continued)

*Primary Examiner* — Thomas McEvoy
(74) *Attorney, Agent, or Firm* — One LLP; Jonathan Jaech (57) ABSTRACT

A dermabrasion device includes an ergonomically contoured handle divided into at least two articulating sections separated by an annular cam ring, wherein each of the at least two articulating sections are coupled to one another and rotatable around a longitudinal axis of a longer one of the at least two articulating sections, whereby a distal end of the handle is displaced from the longitudinal axis. The device further includes an air pump disposed in at least one of the at least two articulating sections configured to draw air through the distal end of the handle, and a mount positioned at the distal end configured for mounting a dermabrasion tip around a channel leading to an inlet of the air pump.

18 Claims, 11 Drawing Sheets

Related U.S. Application Data (60) Provisional application No. 61/866,995, filed on Aug. 16, 2013.

(51) Int. Cl.
*A61B 17/00* (2006.01)
*A61B 17/29* (2006.01)

(52) U.S. Cl.
CPC .............. *A61B 2017/00734* (2013.01); *A61B 2017/2929* (2013.01); *A61B 2017/320004* (2013.01)

(56) References Cited

U.S. PATENT DOCUMENTS

| | | |
|---|---|---|
| 2,499,933 A | 3/1950 | Smul |
| 2,552,485 A | 5/1951 | Howard et al. |
| 2,655,146 A | 10/1953 | Force, Jr. |
| 2,701,559 A | 2/1955 | Cooper |
| 2,712,823 A | 7/1955 | Kurtin |
| 2,746,461 A | 5/1956 | Bocchino |
| 2,867,214 A | 1/1959 | Wilson |
| 2,881,763 A | 4/1959 | Robbins |
| 2,921,585 A | 1/1960 | Schumann |
| 3,214,869 A | 11/1965 | Stryker |
| 3,495,359 A | 2/1970 | Smith |
| 3,964,212 A | 6/1976 | Karden |
| 4,378,804 A | 4/1983 | Cortese, Jr. |
| 4,438,767 A | 3/1984 | Nelson |
| 4,459,987 A | 7/1984 | Pangburn |
| 4,572,187 A | 2/1986 | Schetrumpf |
| 4,655,743 A | 4/1987 | Hyde |
| 4,776,862 A | 10/1988 | Wiand |
| 4,788,769 A | 12/1988 | Maruyama |
| 4,937,984 A | 7/1990 | Taranto |
| 4,945,686 A | 8/1990 | Wiand |
| 4,957,747 A | 9/1990 | Stiefel |
| 4,964,243 A | 10/1990 | Reiter |
| 5,007,206 A | 4/1991 | Paterson |
| 5,012,797 A | 5/1991 | Liang et al. |
| 5,037,431 A | 8/1991 | Summers et al. |
| 5,037,432 A | 8/1991 | Molinari |
| 5,100,412 A | 3/1992 | Rosso |
| 5,122,153 A | 6/1992 | Harrel |
| 5,137,098 A | 8/1992 | Raffaelli |
| 5,207,234 A | 5/1993 | Rosso |
| 5,295,982 A | 3/1994 | Schatz |
| 5,456,735 A | 10/1995 | Ellison-Hayashi et al. |
| 5,484,427 A | 1/1996 | Gibbons |
| 5,609,516 A | 3/1997 | Courson et al. |
| 5,624,416 A | 4/1997 | Schatz |
| 5,662,677 A | 9/1997 | Wimmer |
| 5,800,165 A | 9/1998 | Kirsch et al. |
| 5,800,446 A | 9/1998 | Banuchi |
| 5,810,842 A | 9/1998 | Di Fiore et al. |
| 5,817,050 A | 10/1998 | Klein |
| 5,882,201 A | 3/1999 | Salem |
| 5,897,512 A | 4/1999 | Zagame |
| 5,971,999 A | 10/1999 | Naldoni |
| 6,019,749 A | 2/2000 | Fields et al. |
| 6,039,745 A | 3/2000 | DiFiore et al. |
| 6,042,552 A | 3/2000 | Cornier |
| 6,050,989 A * | 4/2000 | Fox .................. A61B 17/32002 285/184 |
| 6,062,229 A | 5/2000 | Kandratavich |
| 6,120,512 A | 9/2000 | Bernabei |
| 6,139,553 A | 10/2000 | Dotan |
| 6,159,226 A | 12/2000 | Kim |
| 6,178,970 B1 | 1/2001 | Purifoy et al. |
| 6,196,982 B1 | 3/2001 | Ball |
| 6,241,739 B1 | 6/2001 | Waldron |
| 6,277,128 B1 * | 8/2001 | Muldner .............. A61B 17/545 606/131 |
| D448,852 S | 10/2001 | Engelen |
| 6,319,211 B1 * | 11/2001 | Ito ....................... A61M 1/0047 132/320 |
| 6,423,078 B1 | 7/2002 | Bays et al. |
| 6,641,591 B1 | 11/2003 | Shadduck |
| 6,911,031 B2 | 6/2005 | Muldner |
| D511,400 S | 11/2005 | Shubert et al. |
| 6,241,739 C1 | 12/2007 | Waldron |
| D594,130 S | 6/2009 | Scocimara et al. |
| D598,102 S | 8/2009 | Hull, Jr. |
| D613,417 S | 4/2010 | Imboden et al. |
| D623,295 S | 9/2010 | Rhoades et al. |
| D638,935 S | 5/2011 | Gilmore, III et al. |
| D659,106 S | 5/2012 | Paul |
| D672,507 S | 12/2012 | Szymanski |
| D709,617 S | 7/2014 | Iliesco de Grimaldi et al. |
| D716,446 S | 10/2014 | Bitaraf et al. |
| D723,160 S | 2/2015 | Rodan et al. |
| 2004/0138680 A1 | 7/2004 | Twitchell et al. |
| 2004/0254587 A1 | 12/2004 | Park |
| 2009/0222023 A1* | 9/2009 | Boone, III .......... A61B 17/545 606/131 |
| 2012/0209294 A1 | 8/2012 | Bitaraf et al. |
| 2012/0296342 A1 | 11/2012 | Haglund Wendelschafer |
| 2013/0023805 A1 | 1/2013 | Ungemach et al. |

OTHER PUBLICATIONS

International Search Report and Written Opinion dated Jan. 6, 2015 for International Application No. PCT/US2014/051561.

\* cited by examiner

PORTABLE MICRODERMABRASION DEVICE WITH SWIVELING ERGONOMIC HANDLE

CROSS-REFERENCE TO RELATED APPLICATIONS

This application claims priority to U.S. provisional application Ser. No. 61/866,995, filed Aug. 16, 2013, and is a continuation-in-part of U.S. Design patent application Ser. No. 29/477,018 filed Dec. 18, 2013, which applications are specifically incorporated herein, in their entirety, by reference.

FIELD

The present disclosure relates to systems, apparatus and methods for microdermabrasion, including handheld portable devices.

BACKGROUND

Various portable microdermabrasion tools are known in the art, characterized by a dermabrasion tip and a suction motor. The dermabrasion tip may be powered by a rotary motor, or may be static. Suction through the tip may be used to draw in removed skin that is captured in an air filter. An air pump is used to supply suction. Such handheld devices are often designed to be battery powered, and lack suction power. In addition, the devices may be awkward to hold when self-treating lateral or dorsal aspects of the body.

Notwithstanding the advantages of prior dermabrasion devices, there is a need for an esthetically and mechanically improved, simple to operate handheld dermabrasion system useful for the non-professional consumer. The present invention fulfills this need and provides further related advantages, as described below. Reference will be made to the appended sheets of drawings which will first be described briefly.

SUMMARY

A method, system and apparatus for microdermabrasion is presently disclosed. In an aspect, a portable handheld microdermabrasion device includes an ergonomically contoured handle divided into at least two articulating sections separated by an annular cam ring, wherein each of the at least two articulating sections are coupled to one another and rotatable around a longitudinal axis of a longer one of the at least two articulating sections in a plane that is tilted with respect to said axis. In a first position a central axis of the other section holding a dermabrasion tip is generally parallel to and offset from the longitudinal axis by a distance 'R' on order 0.25 to 2.5 inches, for example, 0.6 or 0.75 inches. As the sections are rotated with respect to one another in the rotation plane, a distal end of the handle rotates away from the longitudinal axis to form an acute angle 'A' in the range of about 40° to 90°, for example, 50°, at a second position reached through about 180° of rotation from the first position. The device further includes an air pump disposed in at least one of the at least two articulating sections configured to draw air through the distal end of the handle. In an aspect, the device includes a mount positioned at the distal end configured for mounting a dermabrasion tip around a channel leading to an inlet of the air pump. The longer one of the at least two articulating sections may be configured for gripping.

In related aspects, the dermabrasion device may include a substantially annular dermabrasion tip fixed to the mount. A distal surface of the dermabrasion tip may be configured as a bisected toroid. The bisected toroid may be coated with an abrasive material. The abrasive material may be, or may include, a diamond material.

The dermabrasion device may further include a filter interposed between the dermabrasion tip and the inlet of the air pump. The air pump may be configured to draw at least 3 liters per minute through the channel. An inlet of the air pump may be fluidly coupled to the channel of the dermabrasion tip by a flexible hose. An electric power control circuit disposed in one of the at least two articulating sections may be configured to drive the air pump to draw air through treatment head disposed at the distal end of the handle at varying speeds.

The mount may include a cylindrical outer surface sized to slip inside a cylindrical inner surface of the dermabrasion tip. The cylindrical outer surface may include a double O-ring seal. A second dermabrasion tip may be provided, interchangeable with the dermabrasion tip on the mount.

In an aspect, rotating each of the at least two articulating sections causes the distal end of the handle to move in a substantially elliptical path having a first end substantially aligned with the longitudinal axis and a second end at a point of maximum displacement from the longitudinal axis. When the distal end of the handle is located at the point of maximum displacement, an acute angle may be defined between respective central longitudinal axes of the at least two articulating sections of not less than about 40°.

A more complete understanding of the method, system and apparatus for microdermabrasion will be afforded to those skilled in the art, as well as a realization of additional advantages and objects thereof, by a consideration of the following detailed description of the preferred embodiment. Reference will be made to the appended sheets of drawings, which will first be described briefly.

BRIEF DESCRIPTION OF THE DRAWINGS

In the figures described below, like reference numerals are used to indicate like elements appearing in one or more of the figures.

DETAILED DESCRIPTION

Turning in detail to the drawings, FIGS. 1A-7 show various views of a portable handheld dermabrasion device 100 including an ergonomically contoured handle 101 divided into at least two articulating sections 102, 106 separated by an annular cam ring 104. Each of the at least two articulating sections 102, 106 may be coupled to one another and rotatable (e.g., capable of swiveling) around a longitudinal axis of a longer one 102 of the at least two articulating sections, using any suitable mechanism (not shown), for example, respective interior sleeve bearings around a jointed shaft. Surprisingly, as the articulating sections rotate with respect to one another, the angle between them changes, thereby enabling angle adjustment between a lower one of the sections configured as a grip and an upper one of the sections supporting a dermabrasion tip, through relative rotation around a different axis. In other words, the sections 102, 106 and spacer 104 may be configured with respect to the rotation mechanism such that rotation of the section 106 around the longitudinal axis of section 102 causes a distal end at tip 120 of the handle to be displaced from the longitudinal axis. Interior details regarding the illustrated mechanism for enabling rotation and angle adjustment between the two sections are described below in connection with FIGS. 10-11.

Figure 5:
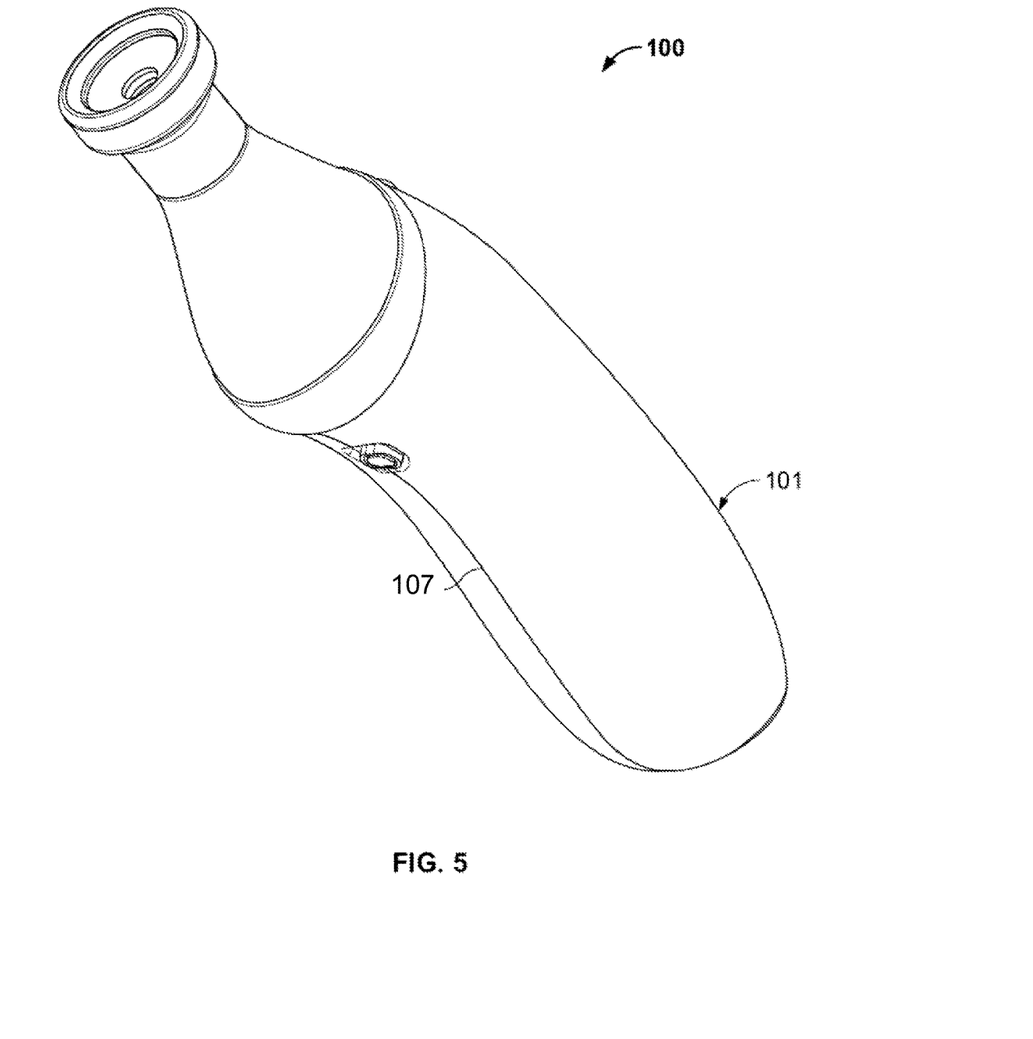
FIG. 5 is an alternative perspective view of the microdermabrasion device.
Figure 6:
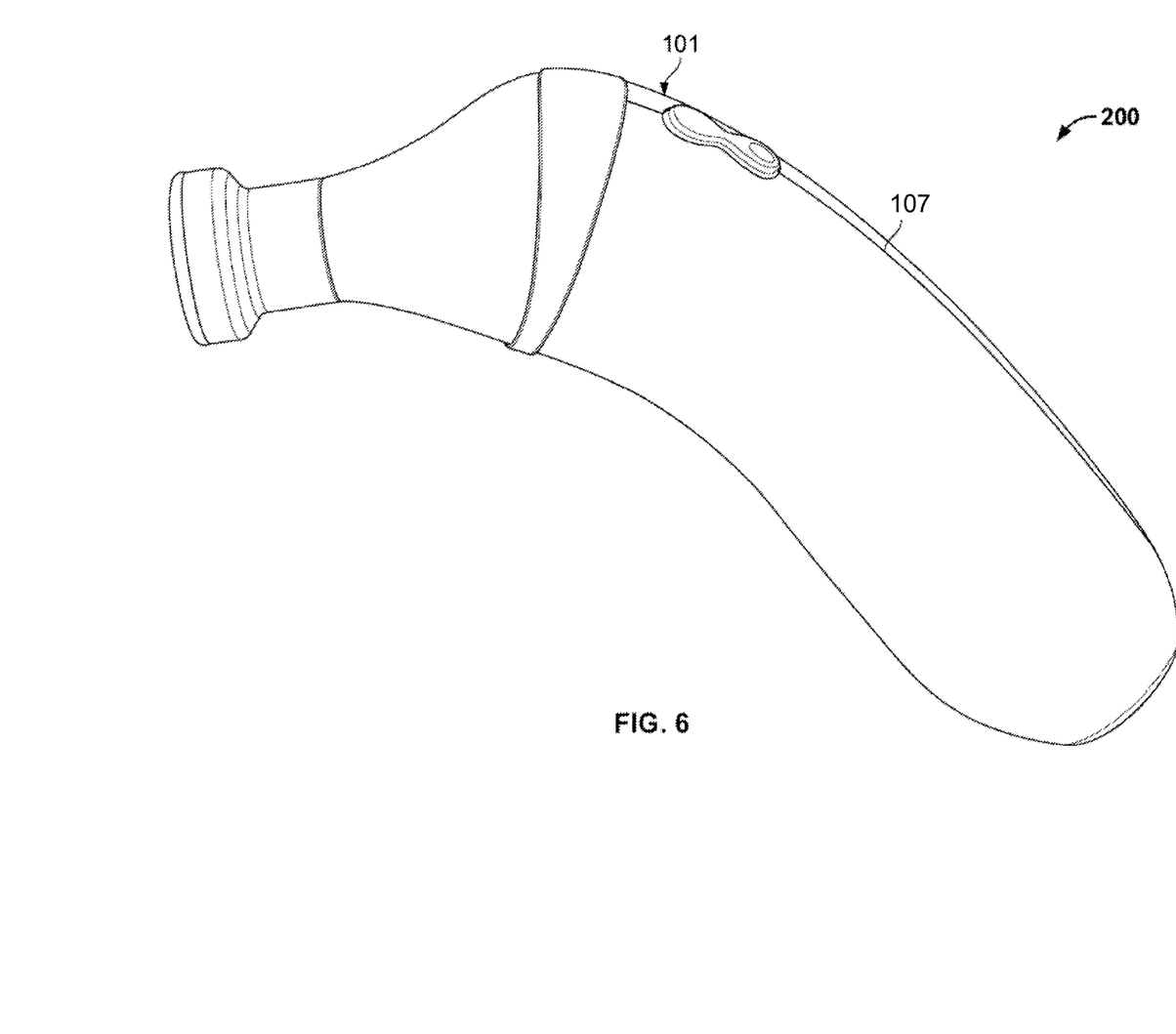
FIG. 6 is another alternative perspective view of the microdermabrasion device, with the upper section in an approximately 90° rotated position relative to the initial position shown in FIG. 2.
Figure 7:
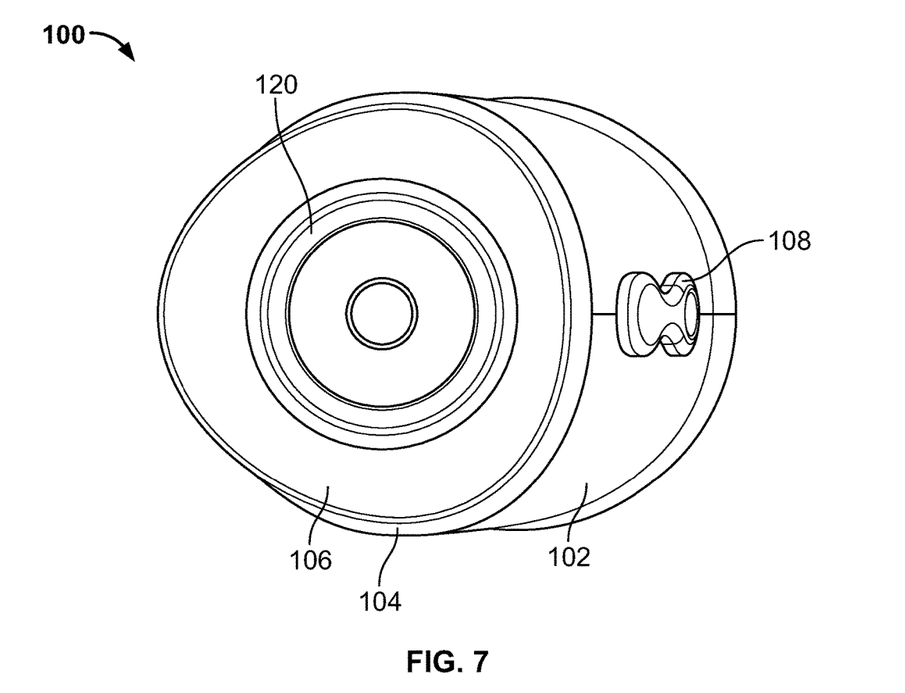
FIG. 7 is an end view of the microdermabrasion device.

FIGS. 5 and 6 show the handle 101 and its join line 107. In the finished device 100, the join line is expected to be nearly invisible or imperceptible, and is therefore not shown on other figures.

FIGS. 1A-7 show the dermabrasion device in a configuration wherein the distal end at the tip 120 is substantially aligned with the longitudinal axis of section 102. This alignment can clearly be seen in FIGS. 2-4. Note there is an offset of about one-half an average radius 'R' of section 102 between a central axis of the tip 120 and a central axis of section 102 as illustrated in the side view of FIG. 2. Any offset between about zero to 'R,' wherein R is a value in the range of about 0.25 to 2.5 inches, should be suitable for a hand held tool. In the illustrated example, 'R' is about 0.6 inch. As used herein, the longitudinal axis of section 102 passes through a center of the base 115 and is perpendicular to the base 115. The longitudinal axis of section 106 passes through the center of the cylindrical abrasive tip 120 and is perpendicular to the plane defined by the tip end 123.

Figures 3, 4:
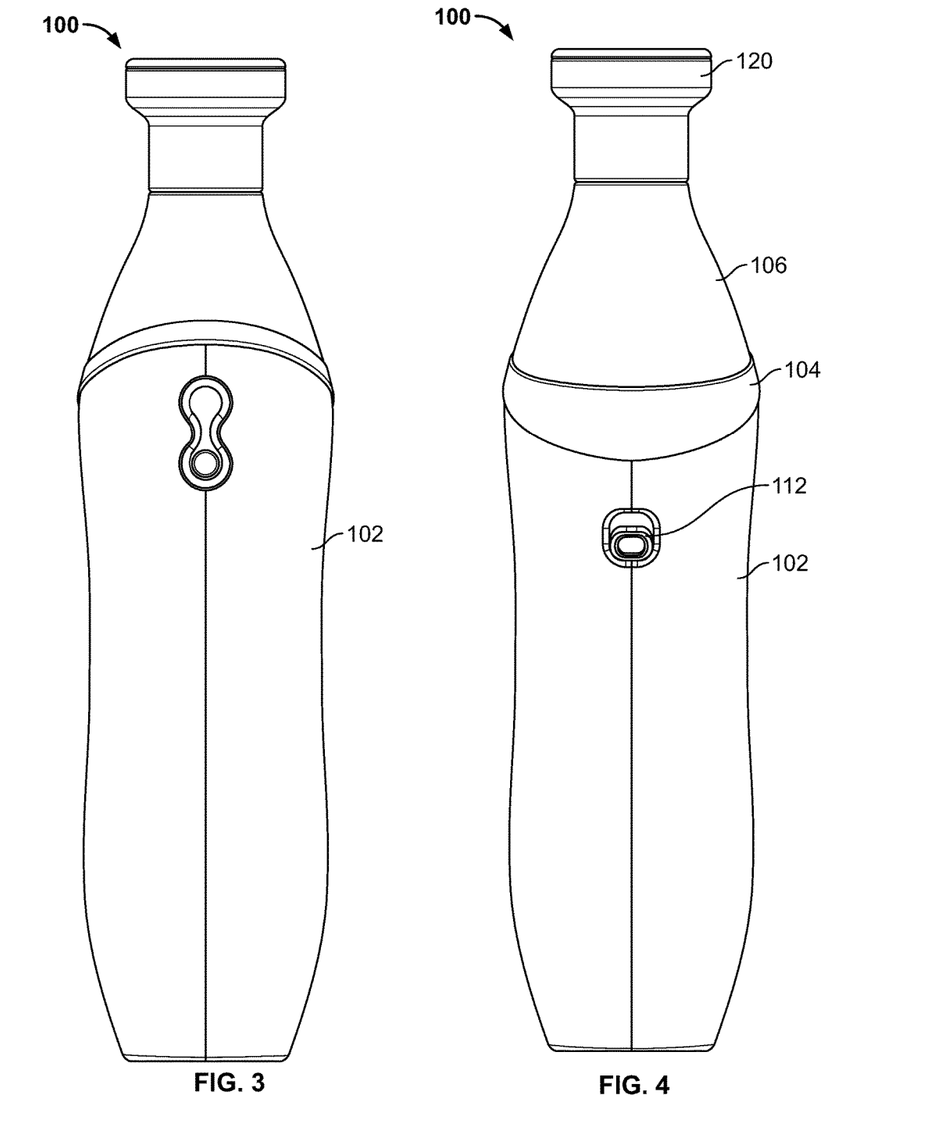
FIG. 3 is a top view of the microdermabrasion device.
FIG. 4 is a bottom view of the microdermabrasion device.

The two sections 102, 106 may be locked into position relative to one another using a locking tab 108, as shown in FIG. 4. When engaged, the tab 108 prevents swiveling of the short handle section 106 relative to the long handle section 102. When disengaged, the sections 102, 106 are free to swivel with respect to one another along a path defined by the cam ring 104 and may lock into place at two or more points along the path, with or without a manually operated locking mechanism such as the locking tab. As used herein, to "swivel" means to rotate. The swiveling mechanism including the cam ring 104 and rotatable section 102, 106 may be adapted for use with similar personal care products, for example, LED Light products used for (red for pain therapy and cell stimulation, and blue for acne treatment, or other colors), buffing/skin cleaning devices, microcurrent-facial stimulation devices, massage devices, hydration devices, hair removal devices, shavers, or other handheld personal care devices. The swiveling mechanism may advantageously improve the versatility and comfort for self-administering the use of a wide range of such personal care devices.

The handle 101 and its components may be made of any suitable structural material, for example structural plastics and/or stainless steel, and may include optional over-molded insets of a rubberized plastic or rubber material (not shown) to enhance grippability. In some embodiments, the over-molded insets may be omitted from the dermabrasion device 100, as shown.

Figure 10:
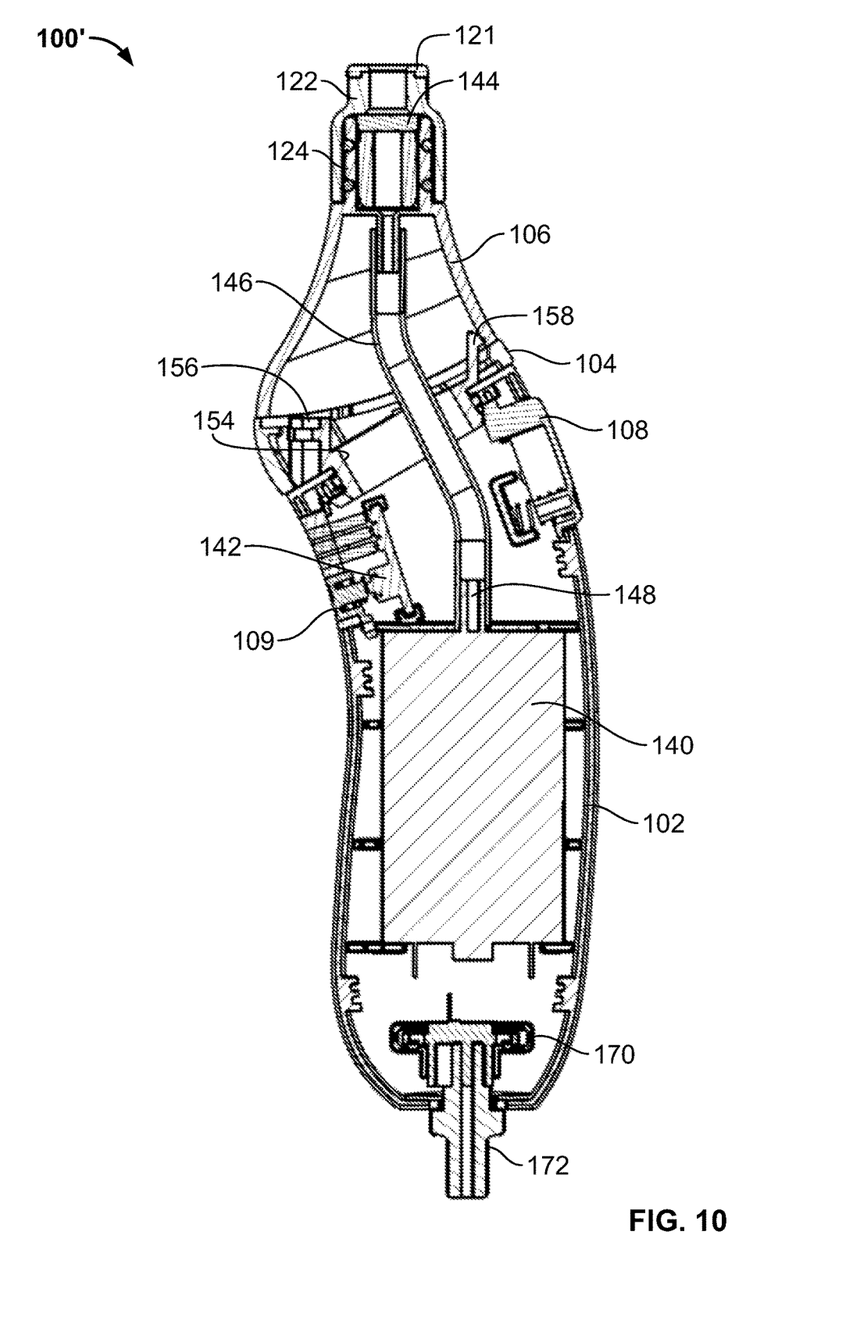
FIG. 10 is a cross-sectional side view of the microdermabrasion device.
Figure 11:
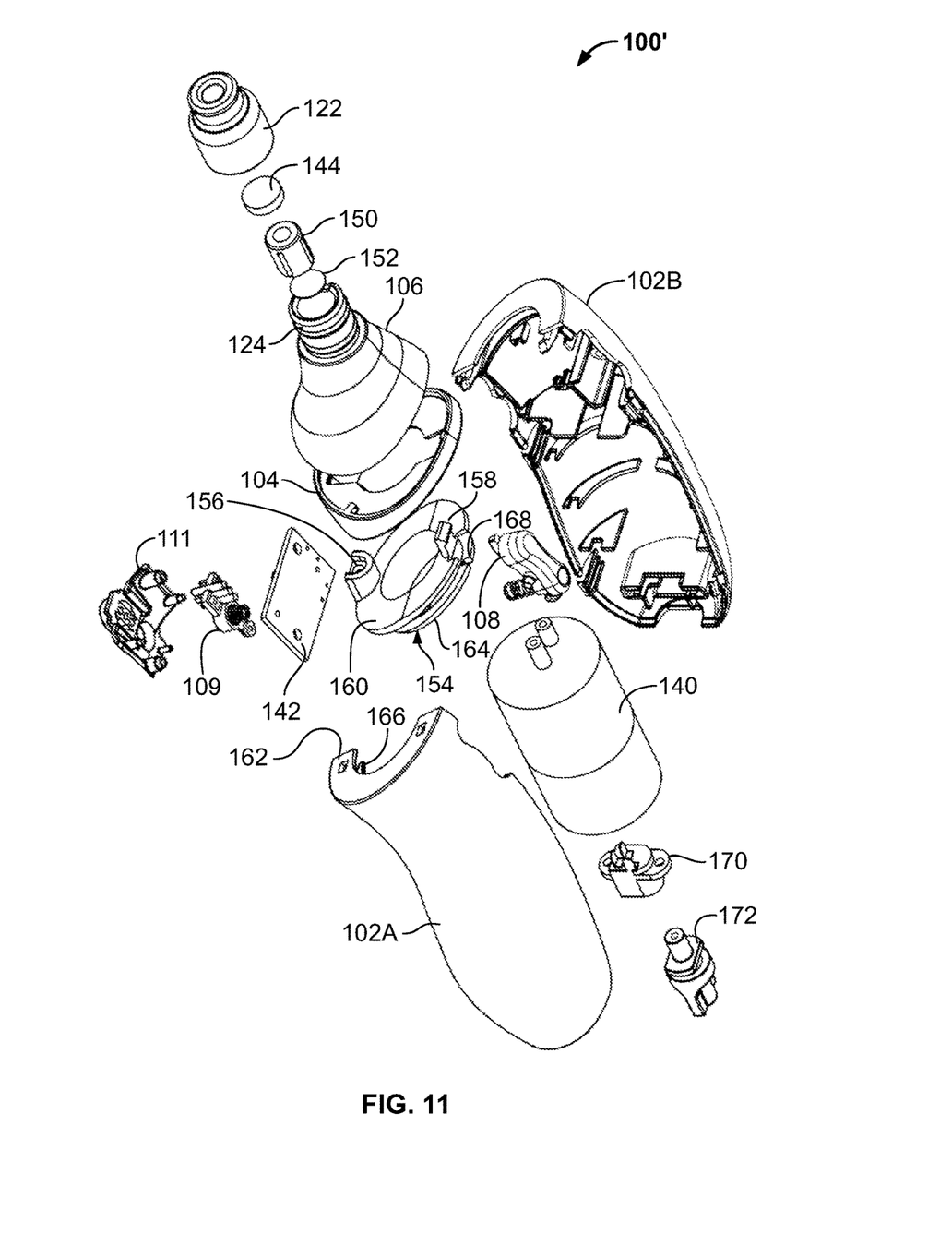
FIG. 11 is another, more detailed perspective view of the microdermabrasion device showing various internal components and details.

The dermabrasion device 100 may include an air pump 140 (FIGS. 10, 11) disposed in one or both of the at least two articulating sections, e.g., longer section 102, configured to draw air through the distal end of the handle. Any suitable air pump may be used. It may be desirable to provide the air pump in a configuration that is not battery powered with a connector (not shown) to a wall outlet. Upper portions of a power connection for a wall outlet, including a connector 170 and strain relief bushing 172, are shown in FIGS. 10-11. The use of external power may enable the device 100 to provide more powerful and consistent suction through the tip 120 than may be possible using battery power. For example, the air pump may be configured to draw air through the channel at a rate of about 3.5 liters per minute, for the illustrated channel size. Battery power may also be used, if desired and suitably powerful.

Power to the air pump may be controlled using a mechanical switch 112 (FIG. 2) or electronic switch 109 (FIG. 1B) on an exterior of the handle 101. The switch 109 or 112 may be configured as a toggle coupled to a timer in electronic circuitry 142 (FIGS. 10, 11), such that, based on the switch 109 or 112 being toggled on, the power to the unit remains on for a definite period of time or indefinitely until the switch is toggled off. Timer-based pump control algorithms may be executed by a microprocessor in circuitry 142 coupled to a timer. A power-on event (e.g., a toggle-on signal) may initiate a timer or counter that counts up and checks the counter value against a constant or user-controlled threshold value, using a program loop. Once the counter reaches or exceeds the threshold value, the loop is terminated and initiates a "power-off" sequence. The power-off sequence may simply cut power or provide an audible or visible signal alerting the user for a predetermined warning period of time (e.g., 1-10 seconds) before power will be shut off, and then cut power if no user input is received during the warning period. If the user toggles the switch during the warning period, the termination sequence may reinitiate the timing loop.

Figure 1A:
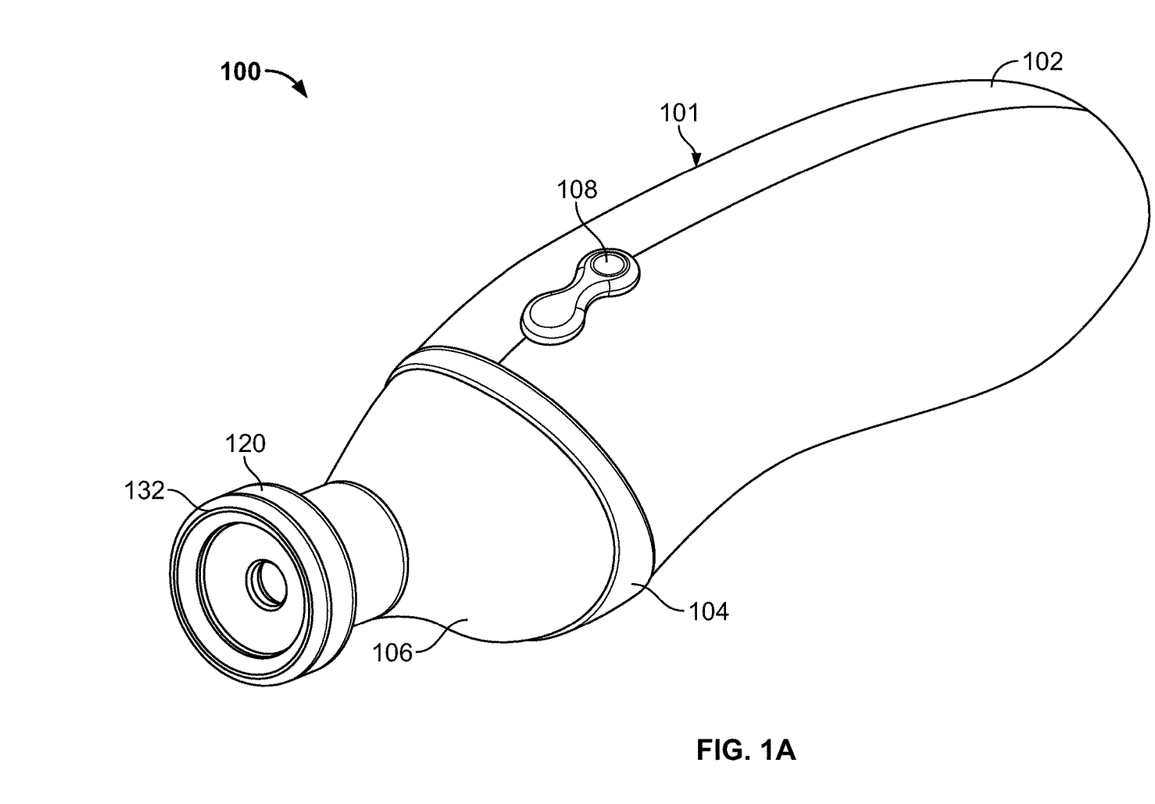
FIG. 1A is a perspective view of a handheld microdermabrasion device with a swiveling ergonomic handle in a configuration with a large tip turned towards a top (lock/unlock switch) side of the device.
Figure 1B:
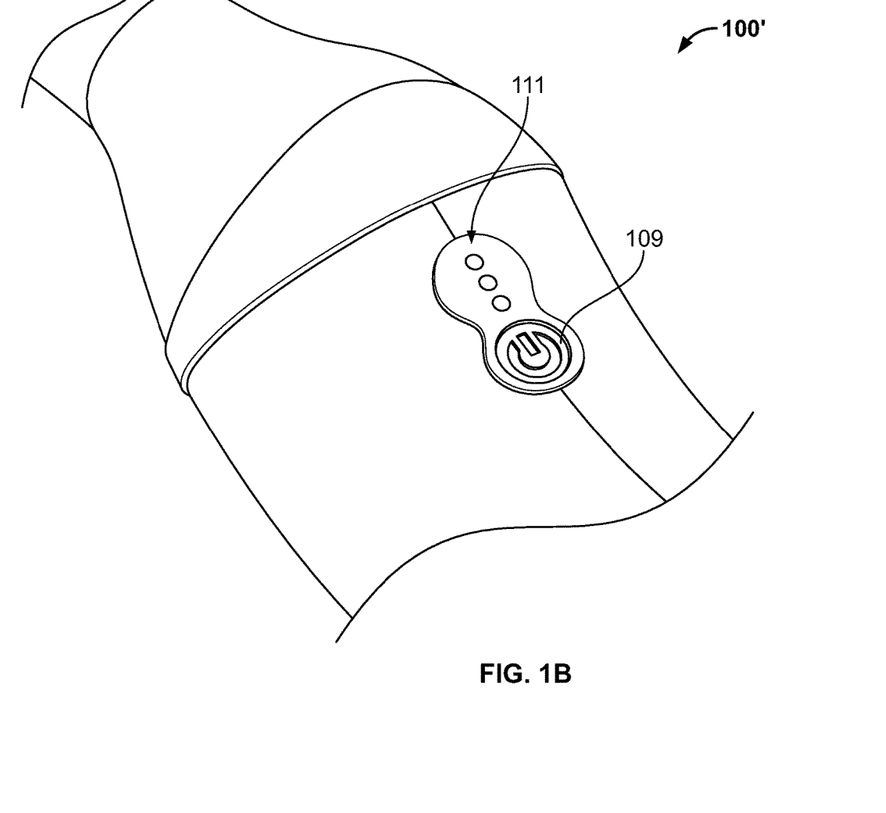
FIG. 1B is a partial perspective view of a handheld microdermabrasion device similar to that shown in FIG. 1A, but with an electronic power switch instead of a mechanical switch.
Figure 2:
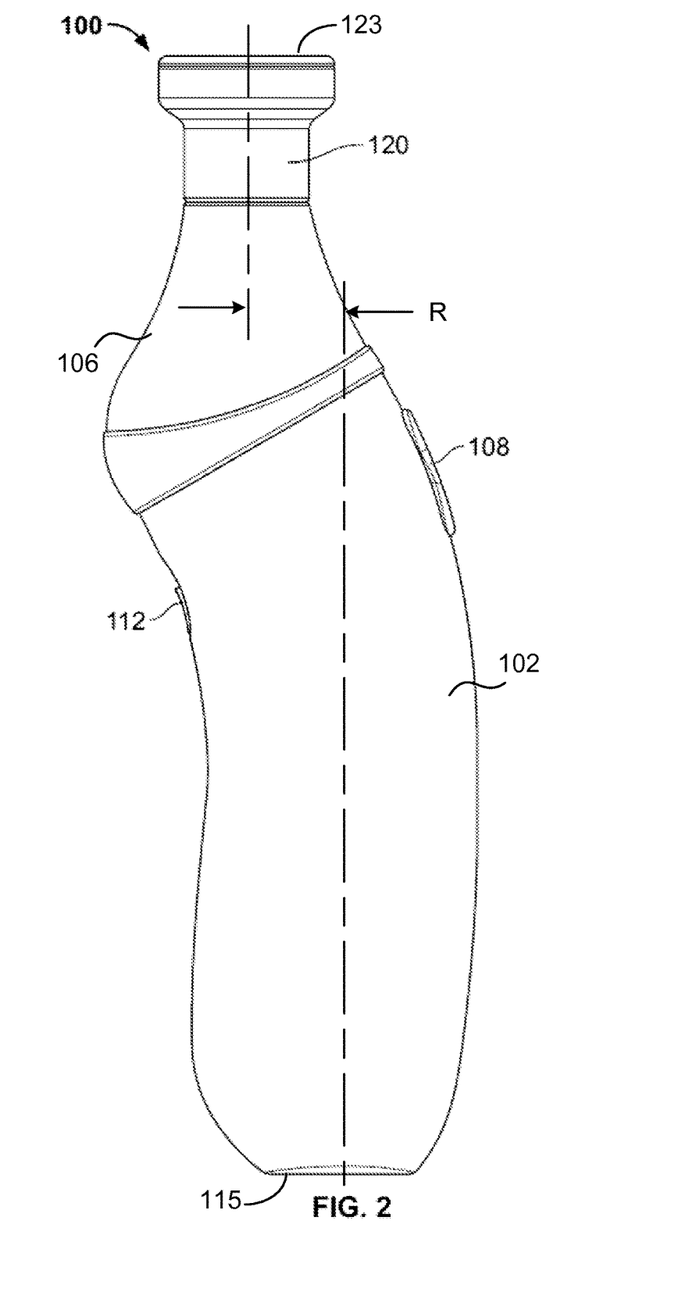
FIG. 2 is a side view of the microdermabrasion device.

Other control functions may be included, for example, to control the speed of the air pump 140 to different speeds between zero (off) and maximum speed, in response to user input. For example, an electronic switch 109 as shown in FIG. 1B on an alternative dermabrasion device 100' otherwise the same as or similar to device 100 may be used in lieu of the mechanical switch 112. The electronic switch 109 may toggle between different pump speeds and power off, with indicator lights on an instrument panel 111 indicating a present speed setting. Pump speed or other operating parameters may optionally be indicated using a control panel of LED's or an LCD display screen. LED indicator lights, for example, are shown assembled to a switch mechanism 109 under the instrument panel 111, in FIG. 11.

A filter 144 (FIGS. 10, 11) may be interposed between the dermabrasion tip 120 and the inlet of the air pump. In the alternative, or in addition, a filter may be interposed between an outlet of the air pump and an exterior of the handle 101. The filter should be designed to be easily removed and replaced. The filter material may be designed to be disposable or washable.

Figure 9:
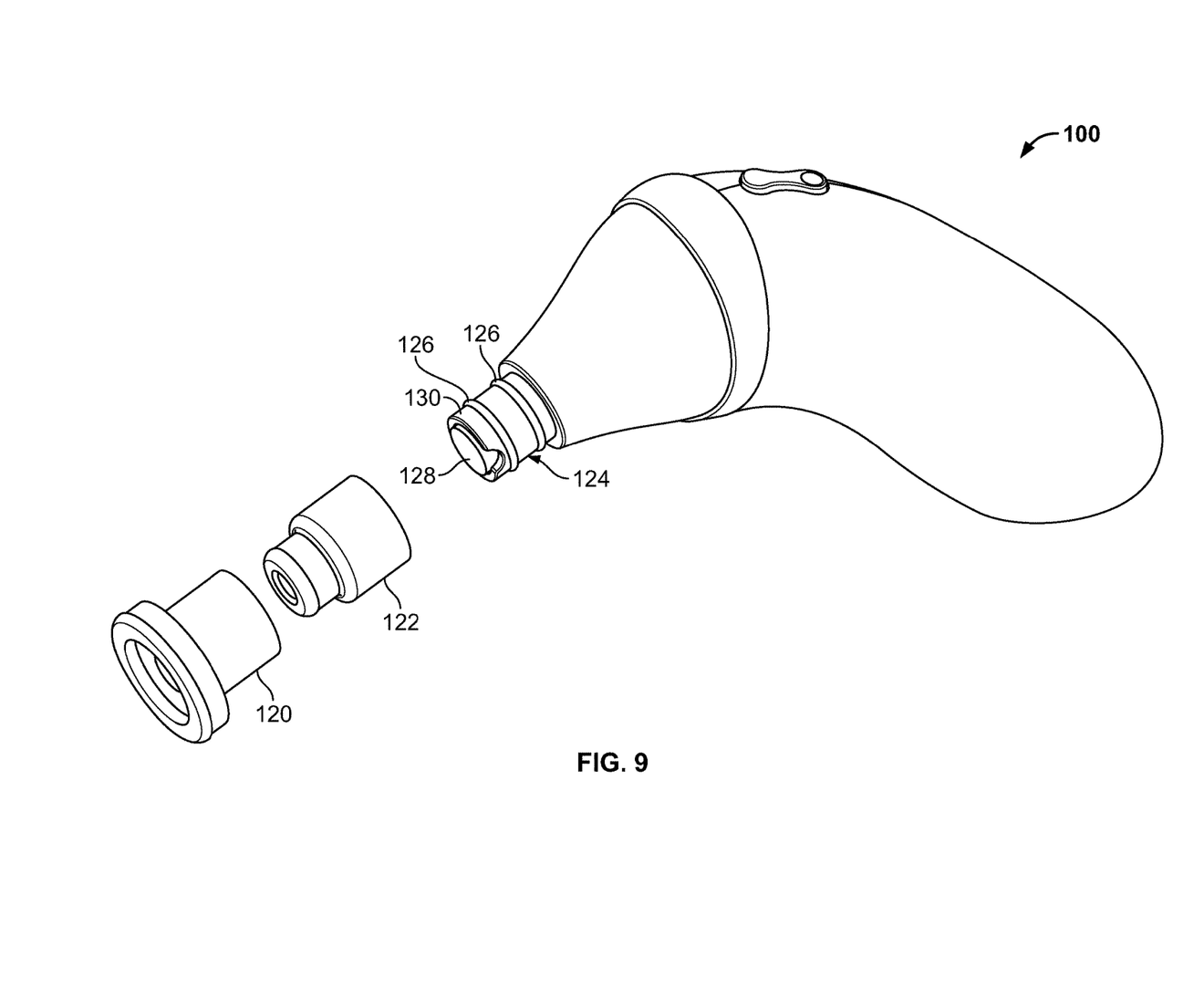
FIG. 9 is an exploded perspective view of the microdermabrasion device showing the large tip and small tip in relation to the rest of the microdermabrasion device.

The dermabrasion device 100 may further include a mount 124, shown in FIG. 9.

The mount 124 may be positioned at the distal end configured for mounting a dermabrasion tip (e.g., one of tips 120, 122) around a channel 128 leading to an inlet of the air pump. The mount 124 may include a cylindrical outer surface 130 sized to slip inside a cylindrical inner surface of the dermabrasion tip, for example, either of tips 120 or 122. The cylindrical outer surface 130 of the mount 124 may include a double O-ring seal, for example dual O-rings 126 disposed in respective O-ring grooves around an outer circumference of the mount 124. The O-rings may provide a dual function by providing frictional resistance holding the dermabrasion tips 120, 122 temporarily in place and sealing the air channel to the air pump inlet, so that all of the suction provided by the air pump is directed to the dermabrasion tip.

The O-rings may provide additional benefits such as cost efficiency, simplicity, durability, and maintainability to the mount 124. Nonetheless, other mounting systems may be used if desired.

Figure 8:
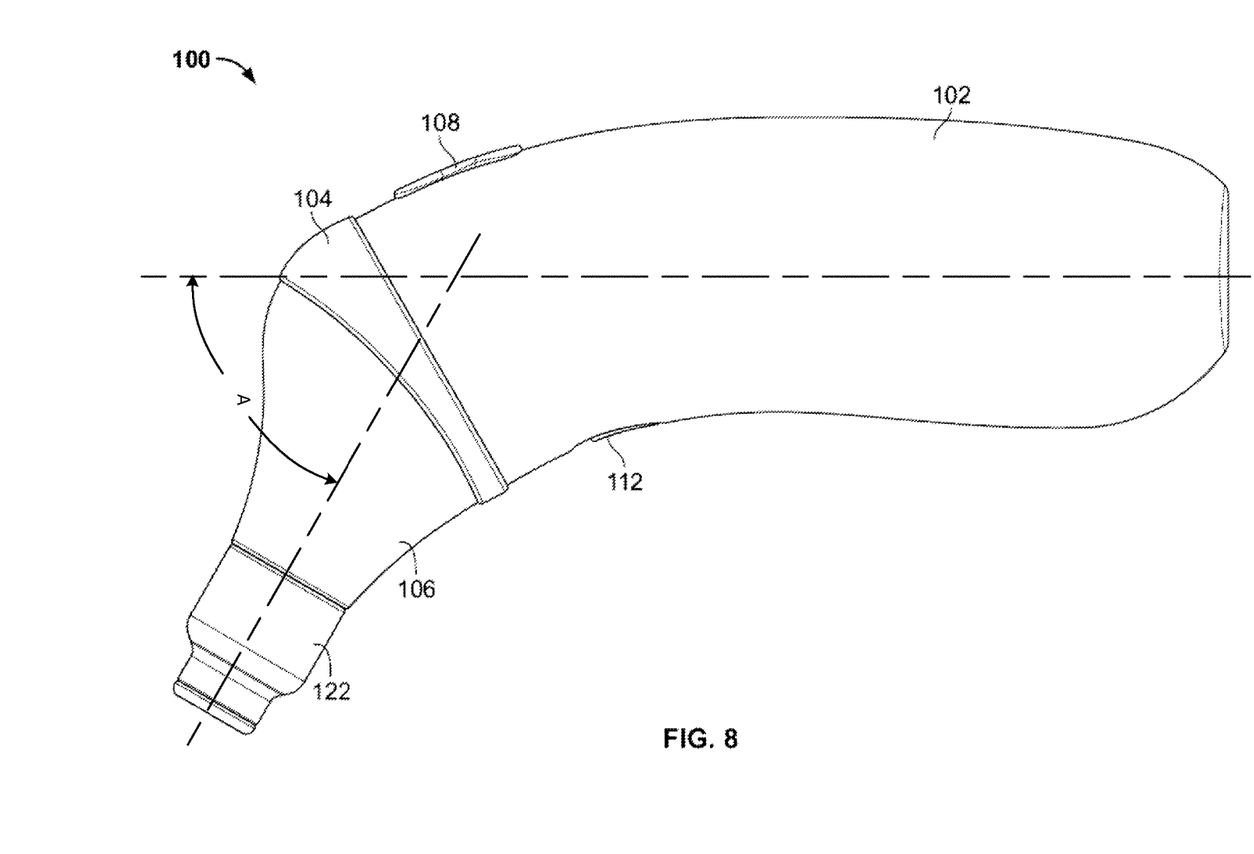
FIG. 8 is a side view of the microdermabrasion device, with a small tip turned towards a bottom (on/off switch) side of the device, rotated approximately 90° from the position shown in FIG. 2.

Referring back to FIGS. 1A-7, the dermabrasion device 100 may include a substantially annular dermabrasion tip 120 removably fixed to the mount. A distal surface 132 of the dermabrasion tip may include a bisected toroid shape. Referring to FIGS. 8-9, the dermabrasion device may be used with a second dermabrasion tip 122 interchangeable with the dermabrasion tip 120 on the mount 124. The bisected toroid surface 132 may be coated with an abrasive material, for example, a diamond powder material bonded to the abrasive surface 121 (FIG. 10) at the distal end of tip 120 or 122.

The second tip 122 or additional tips may be provided in different shapes or sizes, with abrasive surfaces the same as or similar to dermabrasion tip 120. To use the dermabrasion device, the user applies the abrasive tip against her skin, and moves the tip over the skin surface while applying gentle pressure. Meanwhile, the suction provided by the air pump helps to maintain contact between the abrasive surface and the skin, and removes abraded material from the interior of the tip 120 or 122.

Rotating each of the at least two articulating sections with the tab 108 disengaged may cause the distal end of the handle to move in a substantially circular path from a first position in which the longitudinal axes of sections 102 and 106 are substantially parallel to one another and offset from one another, to a second position in which the longitudinal axes of the sections 102 and 106 are at an acute angle to one another. The device 100 in the second position can be seen in the side view of FIG. 8. In the illustrated position of FIG. 8, the dermabrasion device 100 is configured such that an acute angle 'A' is formed between respective central longitudinal axes of the at least two articulating sections of not less than about 40°, for example, as illustrated about 50°. Placing the device 100 in this position may facilitate self-treatment of dorsal or lateral portions of the body, may assist in alleviating wrist fatigue, or both. A user may configure the dermabrasion device 100 in the illustrated position from an initial position illustrated in FIG. 2, by releasing the locking tab 108 and twisting the upper section 106 relative to the lower section 120 about 180° until a rotation stop is reached and the spring-loaded locking tab 108 is re-engaged. The user may restore the dermabrasion device to the position shown in FIG. 2 by reversing these operations.

Referring to FIGS. 10-11, internal aspects of the device 100' are shown in cross-section and exploded views, respectively. An inlet 148 of the air pump 140 is fluidly coupled to an outlet of the mount 124 by a flexible hose or tube 146. The air pump 140 may exhaust to an interior of the lower section 102, which section may be vented with suitable ventilation channels or through holes. Air may be drawn from the tip 122 through the first filter 144, filter body 150 and second filter 152 into the tube 146.

A swiveling and angle adjustment mechanism may include the upper section 102 slideably engaged with the cam ring 104 and lower section 102 by an engagement ring 154. The engagement ring 154 may be fixed to the upper section 106 by a threaded fastener (not shown) engaged at mounting bracket 156 and by clip 158 disposed around the engagement ring 154 approximately 180 degrees from the mounting bracket 156. The engagement ring 154 may be slideably engaged with the lower section 102 by a lower surface of the upper flange 160 held against an outer surface of exterior flange 162 integral to the lower section 102 by the upper surface of the lower flange 164 which is held against a lower surface of the lower flange 166 of section 102. The long section 102 may be assembled from mating halves 102A, 102B by snap engagement and/or threaded fasteners (not shown).

During assembly, the engagement ring 154 may be inserted between the section 102 halves 102A, 102B in the manner shown and described, after being first fixed to the upper section 106 by the mounting bracket 156 and clip 158. The cam ring 104 may thereby be fixed between the engagement ring 154 and the upper section 106. The cam ring 104 is contoured as shown, thereby providing a desired amount of lateral displacement and angle adjustment between the sections 106, 102 when the upper section 106, cam ring 104 and engagement ring 154 are rotated as a body around the lower section 102, as shown and described in connections with FIGS. 2 and 8, herein above. Different amounts of lateral displacement 'R' and angle adjustment 'A' with rotation may be provided for the assembly 100', by substituting a differently-contoured cam ring 104 in the assembly.

The rotation of the sections 106, 102 relative to one another may be circular rotation in a plane tilted with respect to the longitudinal axis shown in FIG. 8. The orientation of the plane of rotation and center of circular rotation may be defined by the interlocking, sliding relationship of the engagement ring flanges 160, 164 and lower section flanges 162, 166 and the circular configuration of these flanges. In a first (parallel) position (FIG. 2) an offset 'R' between central longitudinal axes of sections 102 and 106 is introduced by the curvature of the upper section 106 and the cam ring 104 fixed to the section 106. Being substantially parallel, the angle 'A' between the axes is zero in the first position. In the second (nonparallel) position (FIG. 8), the angle 'A' is increased to approximately 50° by the circular rotation in the tilted plane, essentially converting the offset introduced by the cam ring 104 and section 106 in the first position to the acute angle 'A' between the central longitudinal axes of the sections 102, 106. The locking tab 108 may be engaged with a notch 168 in the lower flange 164 to hold the two sections 102, 106 in a desired rotational position. Similar, additional notches in the flange 164, not visible in the illustrated views, may be provided around the flange 164 to enable locking the sections 102, 106 in place at other rotated positions.

In other aspects, generally with reference to the foregoing figures, the device 100 or 100' may be modified to perform additional or alternative functions related to skin care, or for entirely different applications. For example, a similar personal care device may include an ergonomically contoured handle divided into at least two articulating sections 102, 106 separated by an annular cam ring 104, wherein each of the at least two articulating sections are coupled to one another and rotatable around a longitudinal axis of a longer one of the at least two articulating sections, whereby a distal end of the handle is displaced from the longitudinal axis, the same or similar to the handle 101 of device 100. The similar device may further include an electric power control circuit disposed in one of the at least two articulating sections configured to drive a treatment head (compare tip 120, 122) disposed at the distal end of the handle, wherein the longer one 102 of the at least two articulating sections is configured for gripping.

In an aspect, rotating each of the at least two articulating sections causes the distal end of the handle to move in a substantially elliptical path having a first end substantially aligned with the longitudinal axis and a second end at a point of maximum displacement from the longitudinal axis. When the distal end of the handle is located at the point of maximum displacement, an acute angle may be defined respective central longitudinal axes of the at least two articulating sections that is not less than about 40°.

The treatment head may include a PMD head as described herein above. In alternative aspects, the treatment head may include an LED light skin stimulation lamp (not shown). In another alternative aspect, the treatment head may include a microcurrent facial stimulation effector for skin toning (not shown). In yet another alternative aspect, the treatment head may include a one of a mechanical buffing/skin cleaning head or personal massage head (not shown). In addition, or in the alternative, the treatment head may include a hair clipping or tweezing mechanism, a stimulation hair brush, a powered sun screen applicator for either gel, liquid or aerosol application, or a hydration fluid applicator, all of the foregoing not shown, mounted generally in the location of tips 120, 122.

In one or more exemplary designs, control functions of the described dermabrasion device, for example pump control algorithms, may be implemented in hardware, software, firmware, or any combination thereof. If implemented in software, the functions may be stored as one or more instructions or code on a non-transitory computer-readable medium. Computer-readable media includes computer storage media or any other non-transitory tangible medium that facilitates holding a computer program in storage or machine memory. By way of example, and not limitation, such computer-readable media can comprise RAM, ROM, EEPROM, CDROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Combinations of the above should also be included within the scope of computer-readable media.

Having thus described embodiments of an apparatus, method and system for microdermabrasion using a portable handheld device, it should be apparent to those skilled in the art that certain advantages of the within system have been achieved. It should also be appreciated that various modifications, adaptations, and alternative embodiments thereof may be made within the scope and spirit of the present invention. For example, specific types of dermabrasion tips and specific handle contours been illustrated, but the inventive concepts described above would be equally applicable to implementations with other tips and handle contours. The invention is defined by the following claims.

The invention claimed is:

1. A dermabrasion device, comprising:
an ergonomically contoured handle divided into at least two articulating sections separated by an annular cam ring, wherein each of the at least two articulating sections are coupled to one another by a flanged engagement ring between the cam ring and a longer one of the at least two articulating sections, the engagement ring is slideably engaged with one of the at least two articulating sections by an annular flange held against an outer surface of an exterior flange of the one of the at least two articulating sections and enables rotation of the cam ring and shorter one of the at least two articulating sections around a longitudinal axis of the longer one of the at least two articulating sections, whereby a distal end of the handle is displaced from the longitudinal axis;
an air pump disposed in at least one of the at least two articulating sections configured to draw air through the distal end of the handle; and
a mount positioned at the distal end configured for mounting a dermabrasion tip around a channel leading to an inlet of the air pump.

2. The dermabrasion device of claim 1, further comprising a substantially annular dermabrasion tip fixed to the mount.

3. The dermabrasion device of claim 2, wherein a distal surface of the dermabrasion tip comprises a bisected toroid.

4. The dermabrasion device of claim 3, wherein the bisected toroid is coated with an abrasive material.

5. The dermabrasion device of claim 4, wherein the abrasive material comprises a diamond material.

6. The dermabrasion device of claim 1, further comprising a filter interposed between the dermabrasion tip and the inlet of the air pump.

7. The dermabrasion device of claim 1, wherein the air pump is configured to draw at least 3 liters per minute through the channel.

8. The dermabrasion device of claim 1, wherein the mount comprises a cylindrical outer surface sized to slip inside a cylindrical inner surface of the dermabrasion tip.

9. The dermabrasion device of claim 8, wherein cylindrical outer surface comprises a double O-ring seal.

10. The dermabrasion device of claim 1, further comprising a second dermabrasion tip interchangeable with the dermabrasion tip on the mount.

11. The dermabrasion device of claim 1, wherein rotating each of the at least two articulating sections causes the distal end of the handle to move in a substantially elliptical path having a first end substantially aligned with the longitudinal axis and a second end at a point of maximum displacement from the longitudinal axis.

12. The dermabrasion device of claim 11, wherein when the distal end of the handle is located at the point of maximum displacement, an acute angle between respective central longitudinal axes of the at least two articulating sections is not less than about 40°.

13. The dermabrasion device of claim 11, wherein a central axis of the distal end of the handle is parallel to and offset from the longitudinal axis when the distal end of the handle is at the point of minimum displacement from the longitudinal axis.

14. The dermabrasion device of claim 13, wherein distance of the offset is about one-half an average radius of the handle.

15. The dermabrasion device of claim 1, further comprising a filter interposed between an outlet of the air pump and an exterior of the handle.

16. The dermabrasion device of claim 1, wherein the handle, the annular cam ring, and the engagement ring are made of a structural plastic.

17. A dermabrasion device, comprising:
an ergonomically contoured handle divided into at least two articulating sections separated by an annular cam ring, wherein each of the at least two articulating sections are coupled to one another by a flanged engagement ring between the cam ring and a longer one of the at least two articulating sections, the engagement ring is slideably engaged with one of the at least two articulating sections by an annular flange and enables rotation of the cam ring and shorter one of the at least two articulating sections around a longitudinal axis of the longer one of the at least two articulating sections, whereby a distal end of the handle is displaced from the longitudinal axis;
a mounting bracket and a clip extending from the engagement ring for fastening the engagement ring to the shorter one of the at least two articulating sections;
an air pump disposed in at least one of the at least two articulating sections configured to draw air through the distal end of the handle; and
a mount positioned at the distal end configured for mounting a dermabrasion tip around a channel leading to an inlet of the air pump.

18. A dermabrasion device, comprising:
an ergonomically contoured handle divided into at least two articulating sections separated by an annular cam ring, wherein each of the at least two articulating sections are coupled to one another by a flanged engagement ring between the cam ring and a longer one of the at least two articulating sections, the engagement ring is slideably engaged with one of the at least two articulating sections by an annular flange by an upper surface of a lower flange held against a lower surface of a lower flange of the one of the at least two articulating sections and enables rotation of the cam ring and shorter one of the at least two articulating sections around a longitudinal axis of the longer one of the at least two articulating sections, whereby a distal end of the handle is displaced from the longitudinal axis;
an air pump disposed in at least one of the at least two articulating sections configured to draw air through the distal end of the handle; and
a mount positioned at the distal end configured for mounting a dermabrasion tip around a channel leading to an inlet of the air pump.

* * * * *